US009874521B2

(12) United States Patent
Nagatomi (10) Patent No.: US 9,874,521 B2
(45) Date of Patent: Jan. 23, 2018

(54) DETECTION PLATE (71) Applicant: Panasonic Intellectual Property Management Co., Ltd., Osaka (JP)

(72) Inventor: Kenji Nagatomi, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/909,281

(22) PCT Filed: Aug. 19, 2014

(86) PCT No.: PCT/JP2014/004224
§ 371 (c)(1),
(2) Date: Feb. 1, 2016

(87) PCT Pub. No.: WO2015/029375
PCT Pub. Date: Mar. 5, 2015

(65) Prior Publication Data
US 2016/0178523 A1    Jun. 23, 2016

(30) Foreign Application Priority Data
Aug. 29, 2013  (JP) .................. 2013-177637

(51) Int. Cl.
*G01N 21/64* (2006.01)
*B01L 3/00* (2006.01)
(Continued)

(52) U.S. Cl.
CPC .......... *G01N 21/6452* (2013.01); *B01L 3/502* (2013.01); *B01L 3/5027* (2013.01);
(Continued)

(58) Field of Classification Search
CPC ........... G01N 15/1459; G01N 15/1434; G01N 21/6428; B01L 3/502; B01L 3/5027; B01L 3/545
(Continued)

(56) References Cited
U.S. PATENT DOCUMENTS 5,922,617 A     7/1999  Wang et al.
6,965,433 B2 * 11/2005  Zoval .................. B01J 19/0046
                                                356/246
(Continued)

FOREIGN PATENT DOCUMENTS

JP    2001-522998    11/2001
JP    2003-262584     9/2003
(Continued)

OTHER PUBLICATIONS

International Search Report of PCT application No. PCT/JP2014/004224 dated Nov. 11, 2014.

*Primary Examiner* — Jill Warden
*Assistant Examiner* — Jacqueline Brazin
(74) *Attorney, Agent, or Firm* — McDermott Will & Emery LLP (57) ABSTRACT A detection plate includes a track region having a bottom surface having a groove provided therein, and a well apart from the track region. The well has a bottom surface. The bottom surfaces of the track region and the well are disposed substantially on a plane. This detection plate detects a specimen rapidly and highly accurately with a simple structure.

18 Claims, 11 Drawing Sheets (51) Int. Cl.
  *G01N 21/05* (2006.01)
  *G01N 15/14* (2006.01)
  *G01N 15/10* (2006.01)
  *G01N 21/07* (2006.01)

(52) U.S. Cl.
  CPC .......... *B01L 3/545* (2013.01); *G01N 15/1434* (2013.01); *G01N 15/1459* (2013.01); *G01N 21/6428* (2013.01); *B01L 2300/021* (2013.01); *B01L 2300/024* (2013.01); *B01L 2300/04* (2013.01); *B01L 2300/0803* (2013.01); *B01L 2300/0806* (2013.01); *B01L 2300/087* (2013.01); *B01L 2300/0848* (2013.01); *B01L 2300/0861* (2013.01); *B01L 2400/0409* (2013.01); *G01N 21/05* (2013.01); *G01N 21/07* (2013.01); *G01N 2015/1006* (2013.01); *G01N 2015/1447* (2013.01); *G01N 2021/6482* (2013.01); *G01N 2201/0415* (2013.01); *G01N 2201/0423* (2013.01)

(58) Field of Classification Search
  USPC ........................................................ 422/407
  See application file for complete search history.

(56) References Cited

U.S. PATENT DOCUMENTS

| | | |
|---|---|---|
| 2004/0090901 A1 | 5/2004 | Katayama |
| 2005/0185569 A1* | 8/2005 | Coombs ................ B01L 3/5027 369/275.4 |
| 2005/0255474 A1 | 11/2005 | Fujita |
| 2006/0275181 A1* | 12/2006 | Takeda .................. B01L 3/5085 422/400 |
| 2007/0264722 A1 | 11/2007 | Coombs et al. |
| 2009/0219509 A1* | 9/2009 | Nomura ................. G01N 21/55 356/39 |
| 2013/0294980 A1 | 11/2013 | Takahashi et al. |
| 2013/0294981 A1 | 11/2013 | Takahashi et al. |
| 2013/0294982 A1 | 11/2013 | Takahashi et al. |

FOREIGN PATENT DOCUMENTS

| | | |
|---|---|---|
| JP | 2004-093415 | 3/2004 |
| JP | 2004-158118 | 6/2004 |
| JP | 2006-322819 | 11/2006 |
| JP | 2006-349594 | 12/2006 |
| JP | 2010-008190 | 1/2010 |
| WO | 2003/064998 | 8/2003 |

* cited by examiner

DETECTION PLATE

CROSS-REFERENCE TO RELATED APPLICATIONS

This application is a U.S. national stage application of the PCT International Application No. PCT/JP2014/004224 filed on Aug. 19, 2014, which claims the benefit of foreign priority of Japanese patent application 2013-177637 filed on Aug. 29, 2013, the contents all of which are incorporated herein by reference.

TECHNICAL FIELD

The present invention relates to a detection plate used for an optical detection device that detects a specimen, such as a cell.

BACKGROUND ART

It is important especially in medical fields, such as a clinical site, to detect a specimen, such as a cell, containing specific protein or pathogens from a sample containing a large number of cells. A method of detecting cells using a fluorescence detection device is known.

Figure 10:
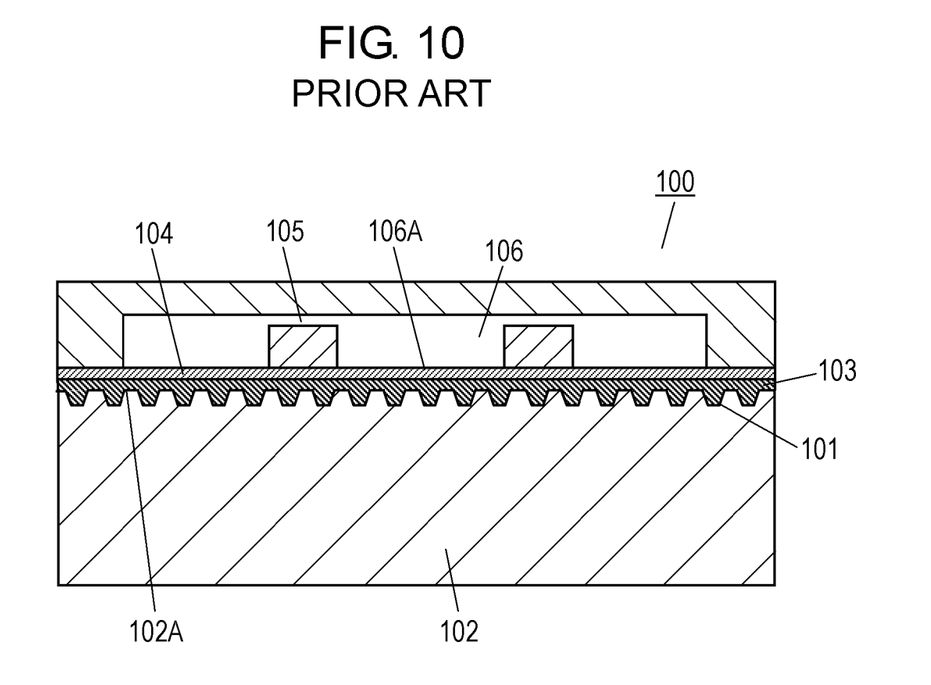
FIG. 10 is a sectional view of a conventional detection plate.

FIG. 10 is a sectional view of conventional detection plate 100 used for a fluorescence detection device. Detection plate 100 includes substrate 102 having track groove 101, reflective layer 103 disposed on substrate 102, active layer 104 disposed on reflective layer 103, flow channel 105 provided in active layer 104, and target region (capture region) 106 provided on active layer 104.

A sample is previously dyed with fluorochrome that binds specifically to a specific substance, is introduced to detection plate 100, and moves in flow channel 105. Cells in the sample are captured in target region 106. Fluorescence excitation light is reflected on track groove 101, and the focus and track position of the fluorescence excitation light are controlled based on a state of the reflected light. The dyed cells emit fluorescence due to the fluorescence excitation light. The intensity of a fluorescence detection signal obtained by the detection of the fluorescence determines the presence of a specific substance.

Detection plate 100 needs irradiation of different light spots when a specimen is fluorescence-excited and detected.

A conventional detection plate similar to detection plate 100 is disclosed in, e.g. PTLs 1 and 2.

CITATION LIST

Patent Literature

PTL 1 WO03/064998
PTL 2 Japanese Patent Laid-Open Publication No. 2004-93415

SUMMARY

A detection plate includes a track region having a bottom surface having a groove provided therein, and a well apart from the track region. The well has a bottom surface. The bottom surfaces of the track region and the well are disposed substantially on a plane.

This detection plate can detect a specimen rapidly and accurately with a simple structure.

DETAIL DESCRIPTION OF PREFERRED EMBODIMENT

Figure 1:
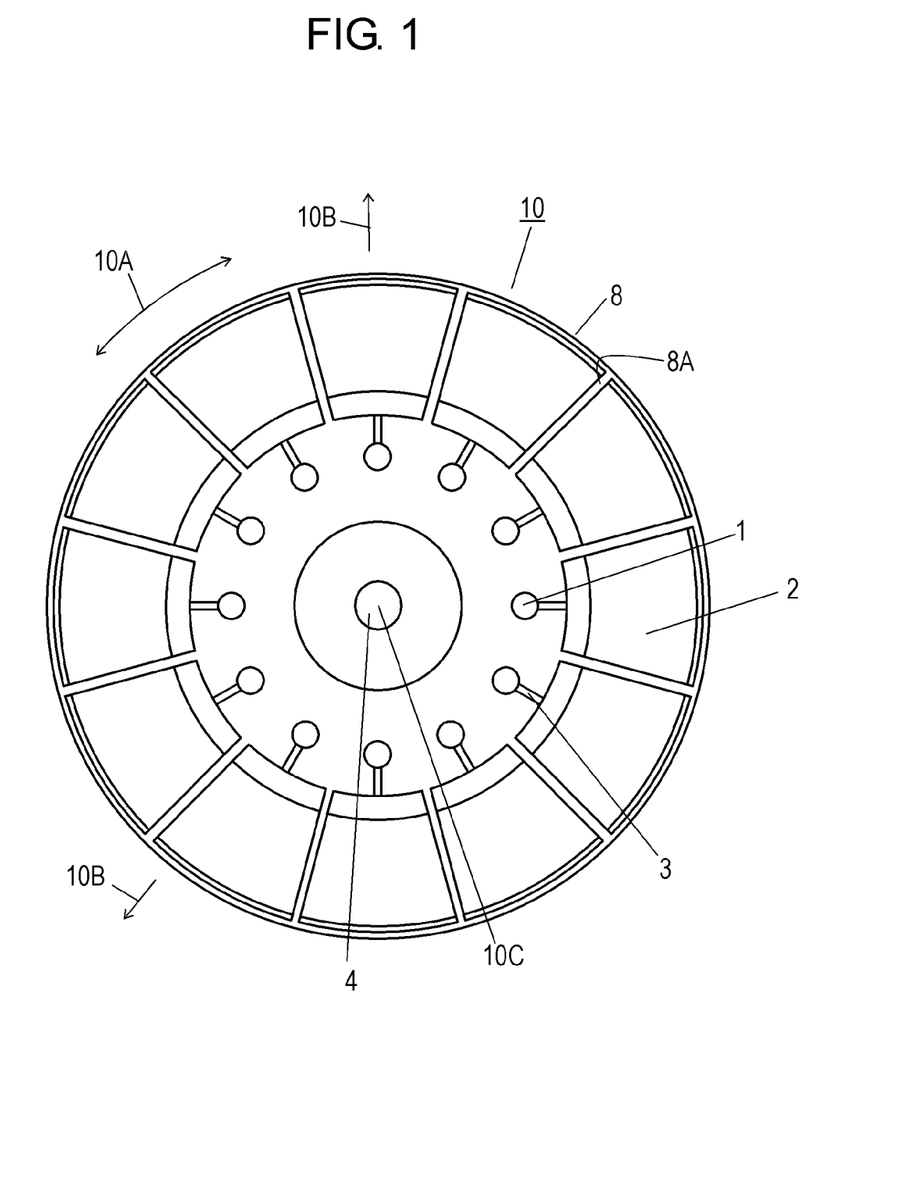
FIG. 1 is a top view of a detection plate according to an exemplary embodiment.

FIG. 1 is a top view of detection plate 10 according to an exemplary embodiment. Detection plate 10 includes substrate 8 having surfaces 8A and 8B opposite to each other, inlet 1 provided in surface 8A of substrate 8, detection region 2 provided on surface 8A of substrate 8, and flow channel 3 provided in surface 8A of substrate 8. A sample containing a specimen is injected into inlet 1. Flow channel 3 introduces the sample from inlet 1 to detection region 2. The sample injected into inlet 1 is introduced through flow channel 3 to detection region 2. The specimen contained in the sample is detected in detection region 2.

Figure 2:
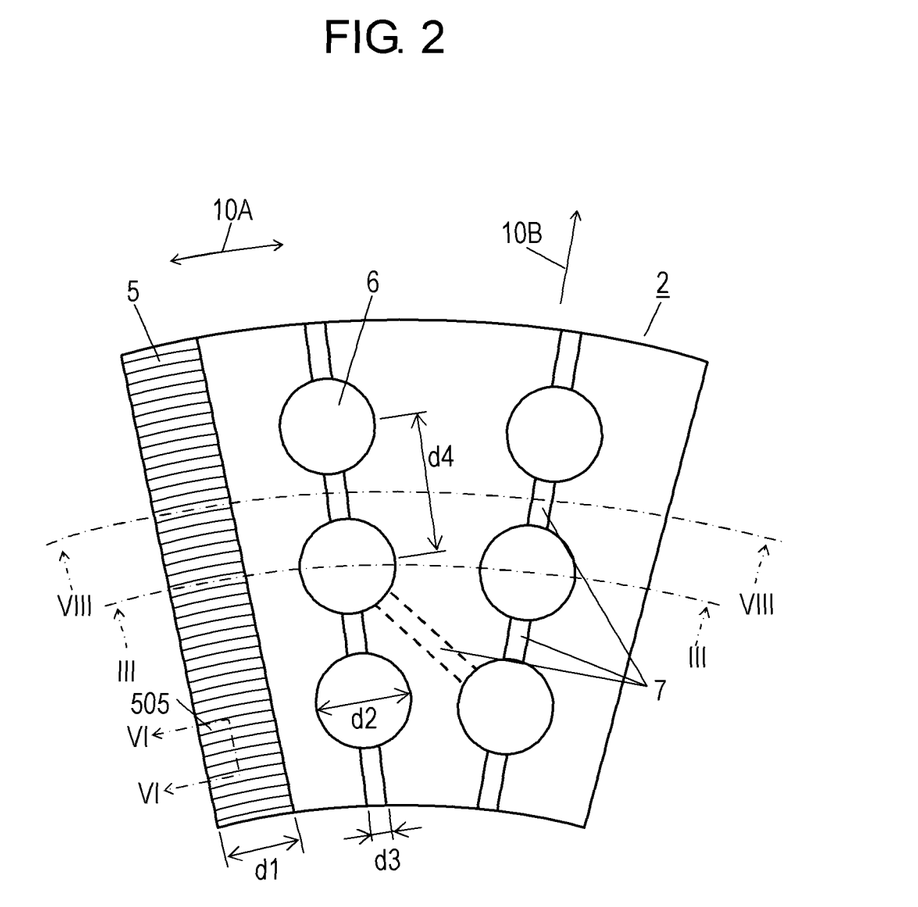
FIG. 2 is a top view of the detection region of the detection plate according to the embodiment.
Figure 3:
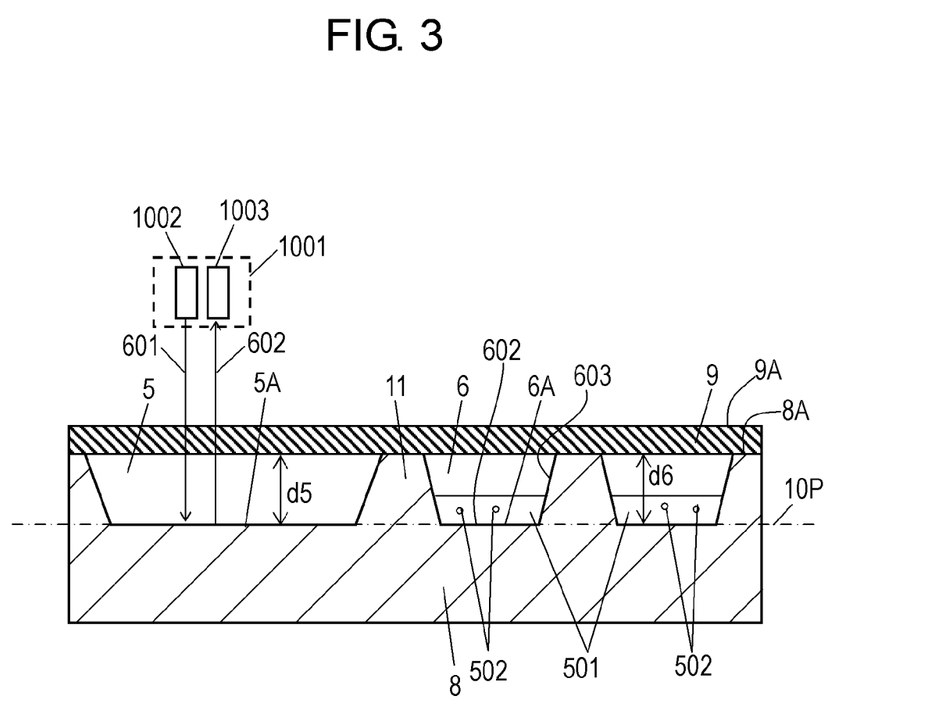
FIG. 3 is a sectional view of the detection region shown in FIG. 2, taken along line III-III.

FIG. 2 is a top view of detection region 2 of detection plate 10. FIG. 3 is a sectional view of detection region 2 along line III-III shown in FIG. 2. Detection region 2 includes track region 5 provided on surface 8A of substrate 8, and well 6 provided on surface 8A of substrate 8. Track region 5 and well 6 are provided on surface 8A, one of surfaces 8A and 8B of substrate 8. Well 6 is configured to accommodate therein sample 501 containing specimen 502. Track region 5 and well 6 are disposed apart from each other.

Track region 5 has bottom surface 5A. Well 6 has bottom surface 6A. Bottom surfaces 5A and 6A of detection plate 10 are disposed substantially on plane 10P. This means that an optical system with a single wavelength can detect bottom surfaces 5A and 6A simultaneously. While the spot of light 601 emitted onto detection plate 10 focuses on bottom surface 5A, the diameter of the spot of light 601 on bottom surface 6A falls within an allowable range required for enough accuracy in detecting fluorescence. Hence, the arrangement of bottom surfaces 5A and 6A changes depending on the wavelength and spot diameter of the light used. The difference between depths d5 and d6 of bottom surfaces 5A and 6A (i.e., the difference between the distance from surface 8A of substrate 8 to bottom surface 5A and the distances from surface 8A of substrate 8 to bottom surface 6A) is defined as offset allowance value $\Delta z$ of bottom surfaces 5A and 6A under the condition that the diameter of the spot of light 601 on bottom surface 6A falls within an allowable range required for enough accuracy in detecting fluorescence. Offset allowance value $\Delta z$ is defined by a spot diameter $w_0$ of light 601 emitted, the wavelength $\lambda$ of light 601, and an allowance value $w(z)$ of the spot diameter as the expression:

$$\Delta z = \{(w(z)/w_0)^2 - 1\} \times \pi \times w_0^2 / \lambda.$$

According to the embodiment, spot diameter $w_0$ is 1 µm, allowance value $w(z)$ of the spot diameter is 1.1 µm, and wavelength $\lambda$ of light 601 is 405 nm. Thus, the above expression provides an offset allowance $\Delta z$ of 3.5 µm according to the embodiment. That is, according to the embodiment, the offset amount (i.e., the difference between depths d5 and d6 of bottom surfaces 5A and 6A positioned substantially on plane 10P) is not larger than 3.5 µm.

In conventional detection plate 100 shown in FIG. 10, surface 102A having track groove 101 is apart from bottom surface 106A of target region 106 in a direction perpendicular to these surfaces. Hence, it is troublesome for an optical system with a single wavelength to control tracking of exciting light within detection plate 100 and to fluorescence-excite and detect a specimen while keeping the optical intensity and irradiation spot diameter to the same extent, and thus light spots different in intensity and diameter need to be emitted.

In detection plate 10 according to the embodiment, bottom surfaces 5A and 6A are positioned substantially on the plane, an optical system with a single wavelength can control tracking and detect specimen 502 while keeping the intensity of light 601 and the spot diameter on bottom surfaces 5A and 6A within respective certain ranges. Thus, detection plate 10 allows an optical system with a single wavelength to detect a specimen rapidly and accurately.

As shown in FIG. 1, substrate 8 of detection plate 10 has a disk shape, similarly to an optical disk, such as a CD and DVD. Hole 4 with a circular shape is provided at center 10C of the disk shape. Detection plate 10 with the disk shape allows an ordinary optical pickup device to detect a specimen.

In detection plate 10, plural detection regions 2 each having track region 5 and well 6 are arranged in a direction in which light is scanned. Plural inlets 1 each connected to respective one of plural detection regions 2 are arranged in circumferential direction 10A of detection plate 10. Plural detection regions 2 on detection plate 10 allow plural specimens to be detected simultaneously with a one-time detection operation. The direction in which light is scanned is circumferential direction 10A of detection plate 10.

The number of detection regions 2 is not especially restricted. Detection region 2 and inlet 1 may be disposed one each. Besides, flow channel 3 may be provided such that one inlet 1 is connected to plural detection regions 2. In the case that inlet 1 is provided on detection region 2, detection plate 10 may not necessarily have flow channel 3.

Detection plate 10 may have a region where sample 501 and a fluorescent reagent are mixed together and/or a region where sample 501 is diffused to detection region 2, between inlet 1 and detection region 2.

Track region 5 and well 6 shown in FIG. 2 are arranged in the direction in which light is scanned on detection plate 10. This arrangement allows stable tracking control by the usage described later as well as specifying well 6 on the basis of positional information captured in track region 5 for efficient acquisition of detection results.

Well 6 has substantially a circular shape. Well 6 having substantially a circular shape allows well 6 to be uniformly filled with sample 501 containing specimen 502. At least one well 6 may be disposed within detection region 2. However, plural wells 6 arranged in radial direction 10B and in circumferential direction 10A of detection plate 10 perpendicular to each other increase the efficiency of detecting specimen 502. Specimen 502 in sample 501 is captured and detected. Plural wells 6 arranged in radial direction 10B of detection plate 10 are connected with flow channel 7. Plural wells 6 connected with flow channel 7 allows sample 501 injected from inlet 1 to be efficiently introduced into plural wells 6 through flow channels 3 and 7 due to, e.g. a centrifugal force.

Flow channel 7 may connect plural wells 6 disposed in circumferential direction 10A of disk-shaped substrate 8 with one another. Flow channel 7 is preferably disposed optimally in order to introduce sample 501 flown to detection region 2 into well 6 efficiently without waste.

According to the embodiment, width d1 of track region 5 is 150 µm. Diameter d2 of well 6 is 100 µm. Width d3 of flow channel 7 is 20 µm. Interval d4 between wells 6 disposed in radial direction 10B or circumferential direction 10A is 200 µm. Each numeric value, however, is to be determined to an optimum value according to some characteristics such as a state of sample 501, the kind of specimen 502, and the hydrophilicity of flow channel 7 and well 6.

Each detection region 2 may not necessarily have wells 6 therein, but may have only one well 6 therein.

Figure 4:
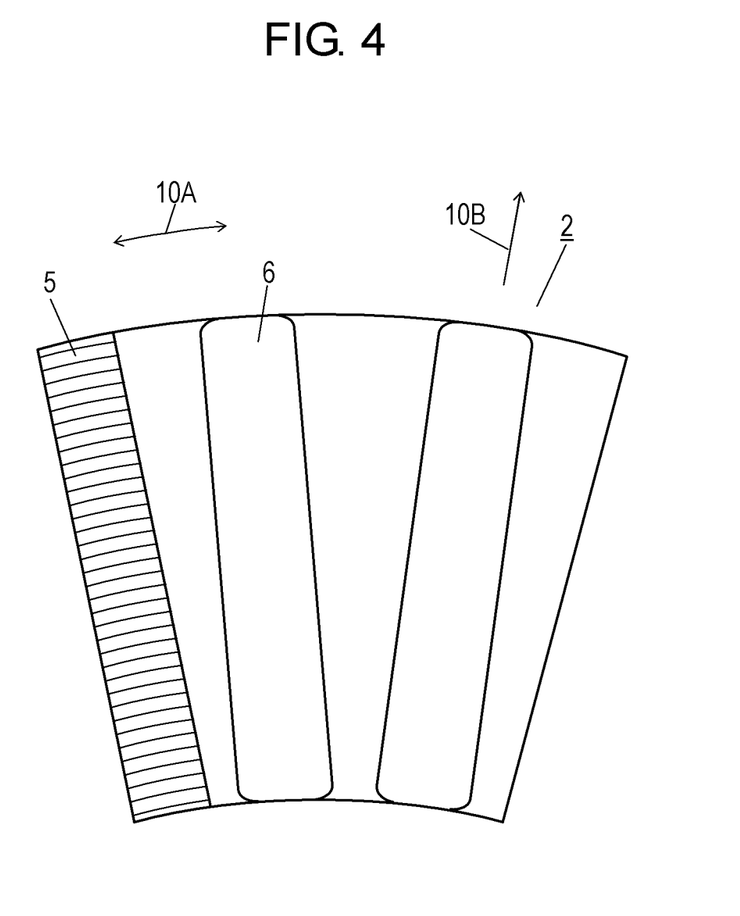
FIG. 4 is a top view of another detection plate according to the embodiment.

The shape of well 6 may not necessarily be substantially a circular shape. Well 6 may have another shape, such as a polygonal or elliptical shape as long as sample 501 can be captured into well 6. FIG. 4 is a top view of another detection region 2 according to the embodiment. As shown in FIG. 4, well 6 may have a shape extending along radial direction 10B of detection plate 10. In this case, flow channel 7 that connects wells 6 arranged in radial direction 10B is not disposed. Detection plate 10 has a different between lengths of the inner and outer circumferences of the disk shape of substrate 8. Well 6 may have a fan shaped having its outer circumference longer than its inner circumference.

Figure 5A:
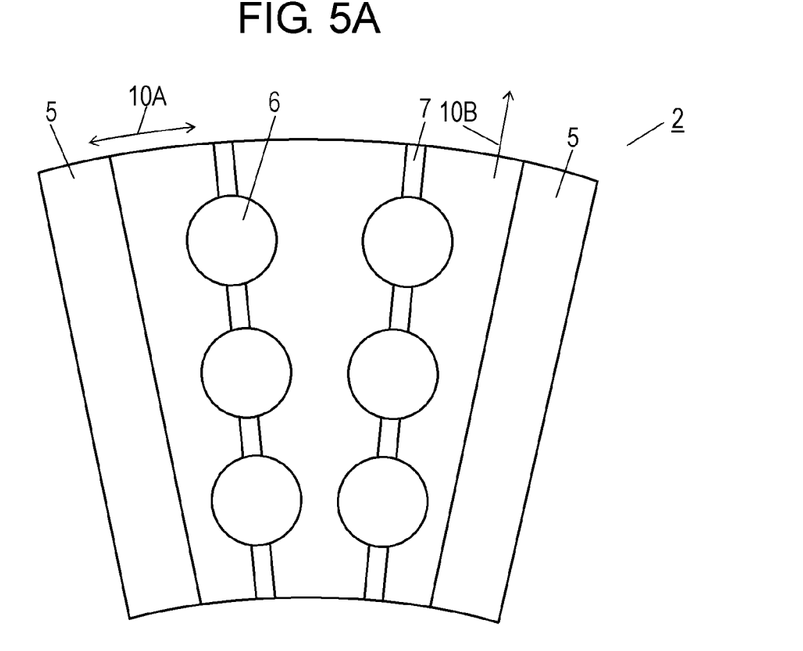
FIG. 5A is a top view of still another detection region according to the embodiment.

FIG. 5A is a top view of still another detection region 2 according to the embodiment. Detection region 2 has plural track regions 5 and plural wells 6. Wells 6 are disposed between track regions 5 in the direction (circumferential direction 10A) in which detection plate 10 is scanned.

Figure 5B:
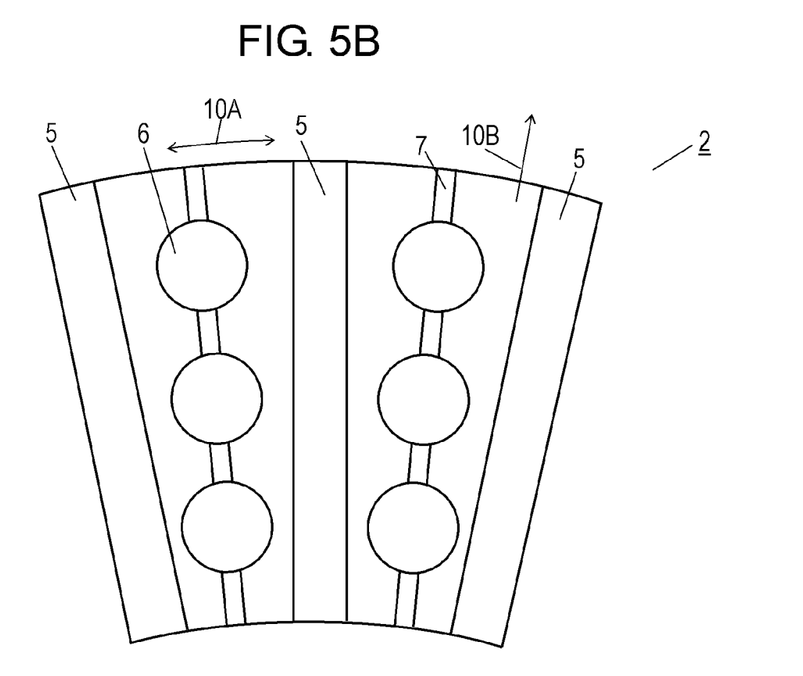
FIG. 5B is a top view of a further detection region according to the embodiment.

FIG. 5B is a top view of still another detection region 2 according to the embodiment. Detection region 2 has plural track regions 5 and plural wells 6. In detection region 2 shown in FIG. 5B, track regions 5 and wells 6 are arranged alternately in the scanning direction (circumferential direction 10A). As shown in FIGS. 5A and 5B, well 6 sandwiched by track regions 5 allows tracking to be controlled more stably by the usage described later to increase the accuracy of detecting a specimen.

Figure 6:
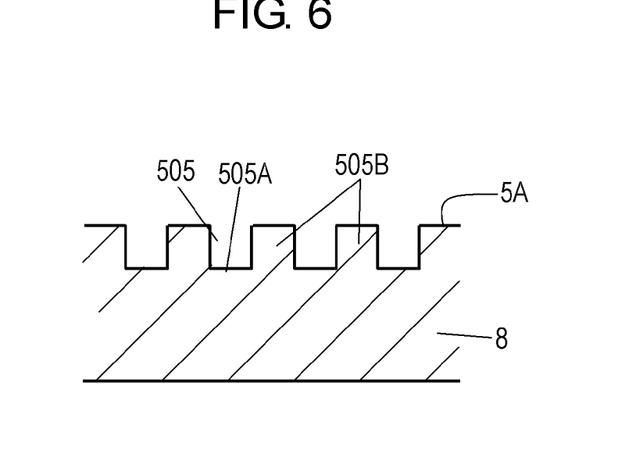
FIG. 6 is a sectional view of the detection plate along line VI-VI shown in FIG. 2.

FIG. 6 is a sectional view of detection plate 10 at line VI-VI shown in FIG. 2. As shown in FIG. 2, bottom surface 5A of track region 5 has track groove 505 therein. As shown in FIG. 6, track groove 505 includes plural lands 505A constituting bottom surface 5A, and groove 505B provided between lands 505A. Track groove 505 has a spiral shape or concentrically circular shapes about center 10C over entire detection plate 10. Track groove 505 according to the embodiment is discontinuous; it may be continuous.

Track groove 505 which is a spiral groove or concentrically circular grooves allows track regions 5 adjacent to one another to be scanned successively, thereby inspecting all well 6.

According to the embodiment, track groove 505 is arranged at pitches of 1 µm and a depth of 40 nm.

Track region 5 may be allocated addresses using pits or wobbles to specify the position of detection plate 10.

Track region 5 may have a reflective film provided on bottom surface 5A. The reflectivity of the reflective film to exciting light ranges, e.g. from 3% to 4%. The reflective film allows freely setting the ratio of the amount of reflected light required for tracking control to the amount of exciting light that transmits through detection plate 10.

Well 6 is a region where specimen 502 in sample 501 is captured and detected. According to the embodiment, depth d6 of well 6 ranges from 10 µm to 50 µm. Bottom surface 6A of well 6 is preferably undergone treatment required for detecting specimen 502. For example, well 6 may have a surface layer made of a resin, such as polydimethylsiloxane (PDMS), provided on bottom surface 6A. In this case, the offset between the surface of the surface layer and bottom surface 5A is not larger than 3.5 µm.

Figure 7:
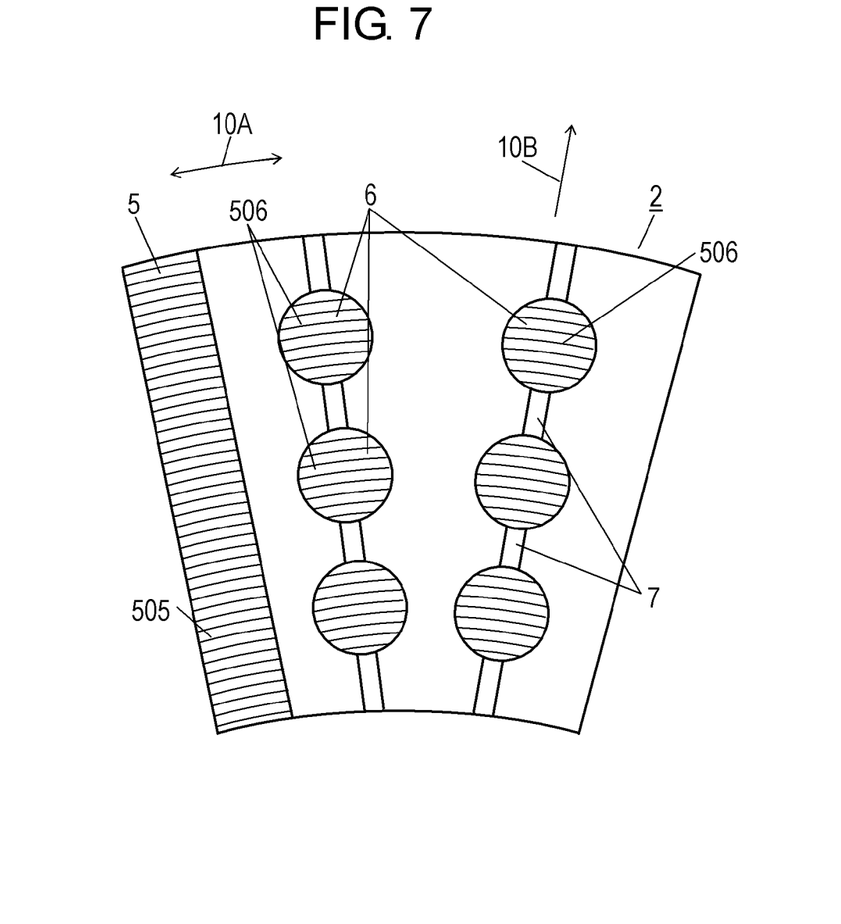
FIG. 7 is a top view of a further detection plate according to the embodiment.

According to the embodiment, a groove may not necessarily be provided in bottom surface 6A of well 6. FIG. 7 is a top view of further detection plate 10 according to the embodiment. In FIG. 7, components identical to those of detection plate 10 shown in FIG. 1 are denoted by the same reference numerals. In detection plate 10 in FIG. 7, groove 506 is provided in bottom surface 6A of well 6. Groove 506 provided in bottom surface 6A allows well 6 to perform tracking control or to detect a tracking control signal, in addition to tracking control in track region 5. Hence, the position of detection plate 10 can be controlled or detected more accurately.

Bottom surface 6A of well 6 may have a solid or planar periodic structure, such as a minute acute shape, the metamaterial structure, and the photonic structure, contributing to the surface plasmon effect. Bottom surface 6A having such a shape allows detection plate 10 to efficiently detect fluorescence.

As shown in FIG. 3, projections 11 are provided between track region and well 6, and between plural wells 6. This structure prevents a sample introduced into well 6 from entering into adjacent wells 6 and/or track region 5 unintentionally. In particular, sample 501 entering into track region 5 may cause unstable tracking control, which makes it troublesome to detect specimen 502 well accurately. Hence, projections 11 provided between track region 5 and well 6 allows specimen 502 to be easily detected accurately.

The height of projection 11 is preferably larger than the diameter of specimen 502 as a detection target. The depth of track groove 505 is preferably smaller than the diameter of specimen 502. This arrangement prevents sample 501 from leaking into track region 5, and even in case of leakage, suppresses its influence on a track control signal.

As shown in FIG. 3, detection plate 10 includes cover layer 9 covering at least well 6 of substrate 8. Sample 501 in detection plate 10 may be dispersed circumferentially due to, e.g. a centrifugal force during a detection operation. To prevent sample 501 from being dispersed, cover layer 9 is desirably formed at least over well 6. Cover layer 9 is provided with a through hole for injection in a region corresponding to the top of inlet 1.

Figure 8A:
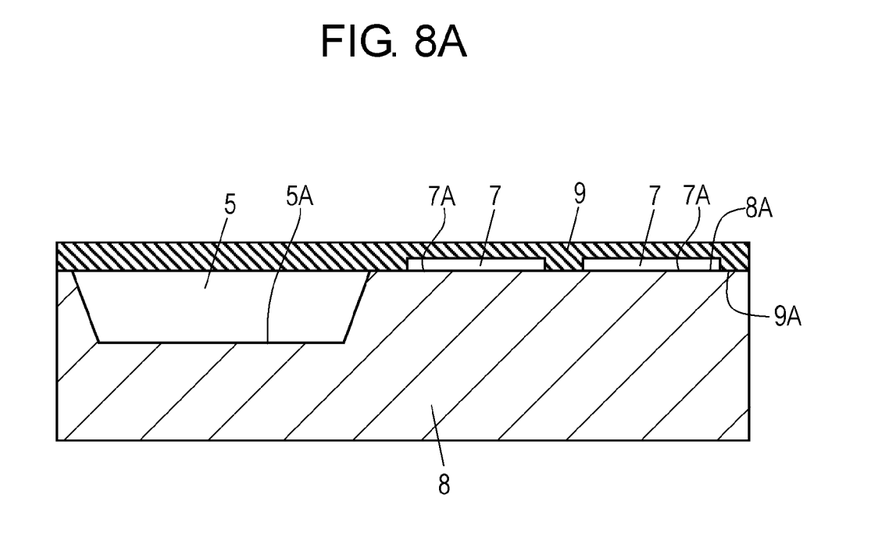
FIG. 8A is a sectional view of the detection region along line VIII-VIII shown in FIG. 2.
Figure 8B:
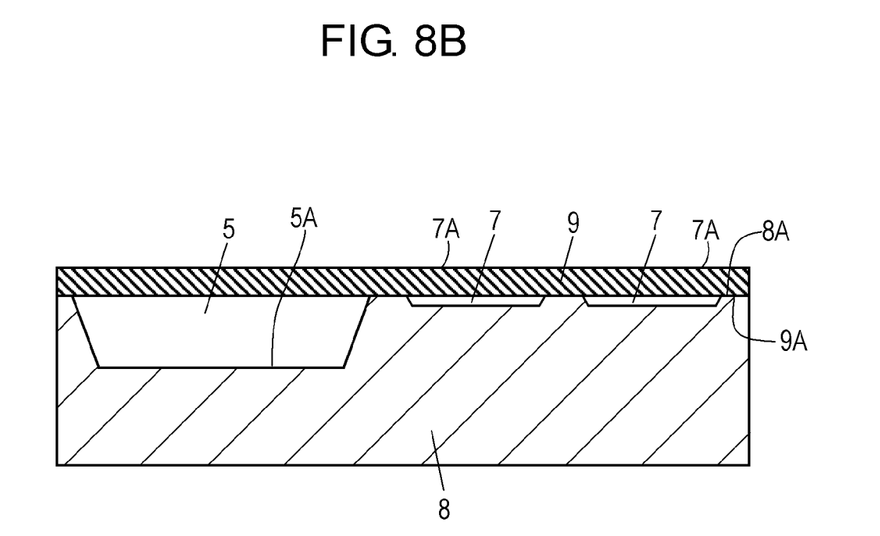
FIG. 8B is a sectional view of the detection region along line VIII-VIII shown in FIG. 2.
Figure 8C:
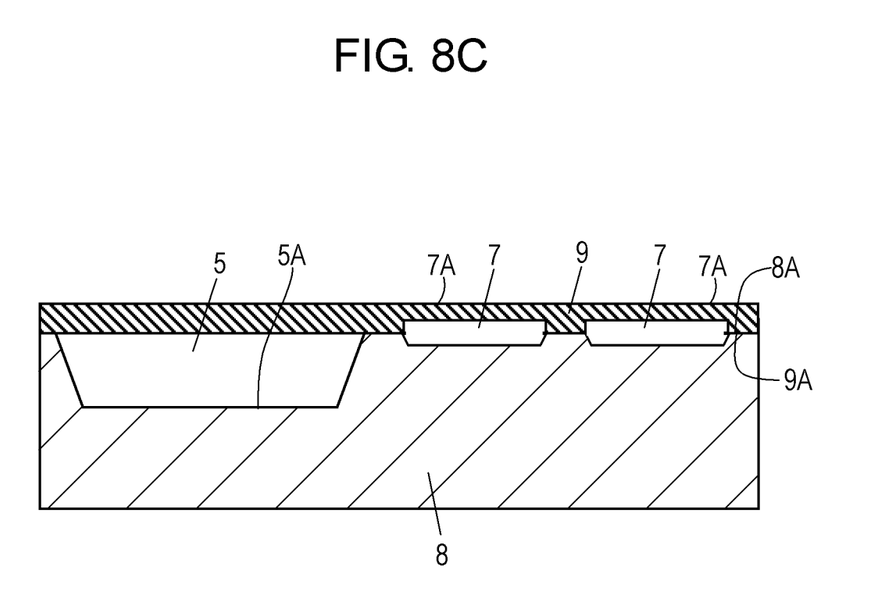
FIG. 8C is a sectional view of the detection region shown in FIG. 2, taken along line VIII-VIII.

FIGS. 8A, 8B, and 8C are sectional views of detection region 2 of detection plate 10 on line VIII-VIII shown in FIG. 2 and show cross sections in circumferential direction 10A. FIGS. 8A, 8B, and 8C illustrate track region 5 and flow channel 7 connecting plural wells 6. Detection plate 10 shown in FIGS. 8A, 8B, and 8C further includes cover layer 9 covering surface 8A of substrate 8. In detection plate 10 shown in FIG. 8A, flow channel 7 is formed on surface 9A of cover layer 9 contacting surface 8A of substrate 8. In detection plate 10 shown in FIG. 8B, flow channel 7 is formed in surface 8A of substrate 8. With detection plate 10 shown in FIG. 8C, flow channel 7 is formed in both surface 8A of substrate 8 and surface 9A of cover layer 9. Flow channel 7 thus can be formed in either one of or both of cover layer 9 and substrate 8 of detection plate 10. Flow channel 7 has bottom surface 7A facing the direction identical to bottom surfaces 5A and 6A of track region 5 and well 6. However, bottom surface 6A of well 6 is preferably provided at a position lower than bottom surface 7A of flow channel 7.

Detection plate 10 captures specimen 502 contained in sample 501 within well 6 to detect it. Hence, bottom surface 6A of well 6 provided at a position lower than bottom surface 7A of flow channel 7 allows specimen 502 contained in sample 501 to be captured in well 6 reliably.

Figure 9A:
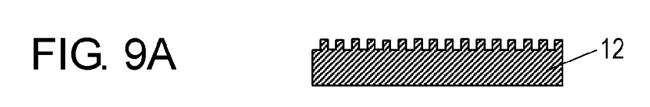
FIG. 9A is a sectional view of the detection plate according to the embodiment for illustrating a method of producing the detection plate.
Figure 9B:
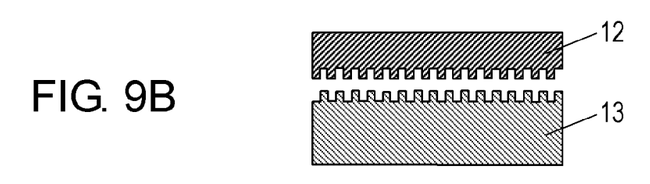
FIG. 9B is a sectional view of the detection plate according to the embodiment for illustrating the method of producing the detection plate.

A method of producing detection plate 10 will be described below. FIGS. 9A to 9G are sectional views of detection plate 10 for illustrating the method of producing detection plate 10. FIGS. 9A and 9B illustrate cross sections of detection plate 10 in radial direction 10B. FIGS. 9C to 9G illustrate cross sections of detection plate 10 in circumferential direction 10A.

The detection plate is formed preferably by unitarily molding track region 5, well 6, flow channels 3 and 7, and inlet 1. Hereinafter, a method of producing detection plate 10 by unitary molding will be described below.

First, as shown in FIG. 9A, master disk 12 for an optical disk, such as a CD and DVD is prepared. As shown in FIG. 9B, master disk 12 is transferred to produce disk substrate 13. Examples of a material of disk substrate 13 include polycarbonate, polymethylmethacrylate, epoxy resin, cyclic olefin resin, and a resin of polylactic acid.

Figure 9C:
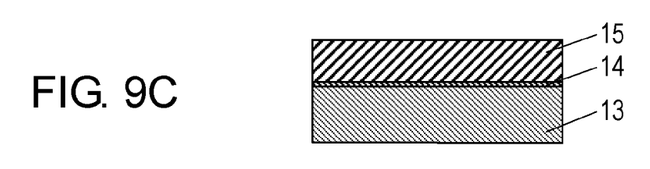
FIG. 9C is a sectional view of the detection plate according to the embodiment for illustrating the method of producing the detection plate.
Figure 9D:
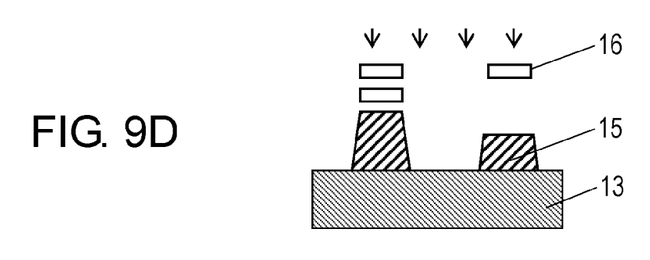
FIG. 9D is a sectional view of the detection plate according to the embodiment for illustrating the method of producing the detection plate.
Figure 9E:
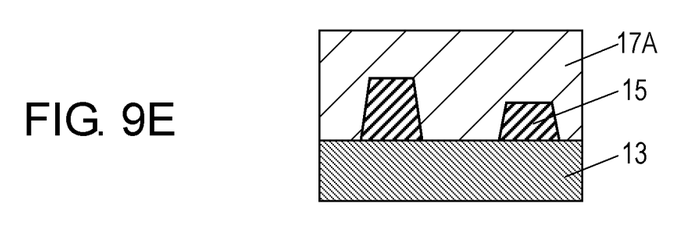
FIG. 9E is a sectional view of the detection plate according to the embodiment for illustrating the method of producing the detection plate.
Figure 9F:
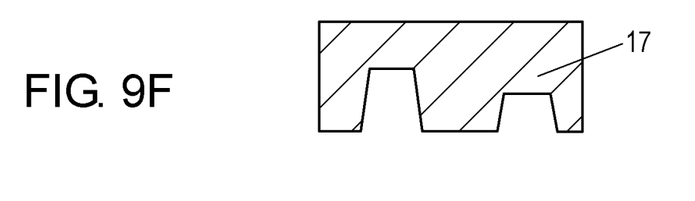
FIG. 9F is a sectional view of the detection plate according to the embodiment for illustrating the method of producing the detection plate.

Next, as shown in FIG. 9C, metal film 14 (e.g., gold or aluminum) is deposited on disk substrate 13 produced as a photoresist support layer as appropriate to form photoresist 15 on metal film 14. Subsequently, as shown in FIG. 9D, mask 16 is formed at the positions of projection 11 and flow channels 3 and 7 of detection plate 10 is exposed, and then, is developed. Further, as shown in FIG. 9E, metal layer 17A is deposited on the disk with mask 16 removed by electroforming. After that, as shown in FIG. 9F, disk substrate 13 and photoresist 15 are removed to produce mold 17 made of metal layer 17A of detection plate 10.

Figure 9G:
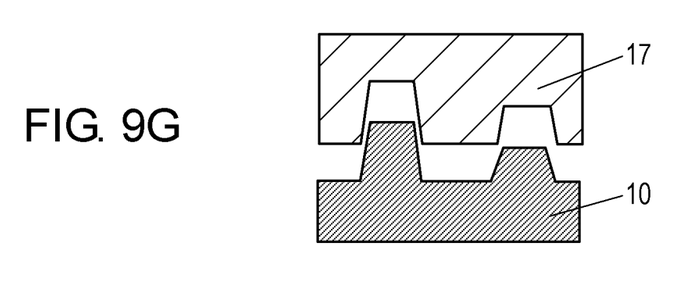
FIG. 9G is a sectional view of the detection plate according to the embodiment for illustrating the method of producing the detection plate.

Then, as shown in FIG. 9G, detection plate 10 can be produced by transferring mold 17 to the material of detection plate 10. Examples of a material of detection plate 10 include polycarbonate, polymethylmethacrylate, epoxy resin, cyclic olefin resin, and a resin of polylactic acid.

Here, detection plate 10 may not be produced by the above-described method (i.e., mold 17 with track groove 505 is produced and then transferred). For example, track groove 505 may be formed in detection plate 10 with track region 5 and well 6 produced thereon with a resin using, e.g. laser. Besides, to produce track region 5 and well 6, a 2P molding technique, or a laminate molding with a three-dimensional printer for instance may be used.

Thus forming track region 5 and well 6 on one continuous plane allows detection plate 10 to be unitarily molded, thereby increasing the positional accuracy of track groove 505 and well 6 in track region 5. The positional accuracy of track groove 505 in track region 5 increased allows the position of fluorescence to be easily identified to allow precise mapping, thereby increasing the detection accuracy. Further, substrate 8 including track region 5 and well 6 of detection plate 10 can be produced by unitary molding, which allows detection plate 10 to be produced in a short time at low cost.

Detection plate 10 is preferably produced by unitarily molding track region 5 and well 6. The production method is not limited to unitary molding as long as bottom surface 5A of track region 5 and bottom surface 6A of well 6 are disposed substantially on plane 10P. For example, detection plate 10 can be produced by disposing a well layer for forming well 6 on a substrate having track groove 505 provided therein. The well layer is made of a resin, such as polycarbonate and PDMS.

A method of using detection plate 10 will be described below.

Sample 501 containing fluorescence-labeled specimen 502 is injected through inlet 1 of detection plate 10. Subsequently, detection plate 10 is set to detection device 1001 (FIG. 3). Detection device 1001 includes light source 1002 and light detector 1003, similarly to an optical pickup device used for recording and playing a CD and DVD. Detection device 1001 rotates detection plate 10 about center 10C. Light source 1002 irradiates surface 8A of rotating detection plate 10 perpendicularly with exciting light 601 (i.e., laser light). Detection device 1001 scans detection plate 10 from an inner circumference to an outer circumference of the plate (or from the outer circumference to the inner circumference) according to the structure of track groove 505 and a rotation direction of detection plate 10, with spots of exciting light 601. Part of light 601 emitted onto detection plate 10 is reflected and led to light detector 1003 as reflected light 602. Detection device 1001 performs focus control and tracking control in track region 5 of detection plate 10 and is controlled so as to detect specimen 502 in sample 501 in well 6. Detection device 1001 includes a control circuit having a sample hold function. For example, exciting light 601 emitted onto detection plate 10 is reflected on bottom surface 5A of track region 5, and reflected light 602 is led to light detector 1003. Detection device 1001 performs tracking control using reflected light 602 reflected on bottom surface 5A. Exciting light 601 emitted onto detection plate 10 causes dyed specimen 502 contained in sample 501 accommodated in well 6 to emit fluorescence. Light detector 1003 to detect the fluorescence emitted from dyed specimen 502 to detect specimen 502 in sample 501. Detection plate 10 with track region 5 and well 6 disposed spaced from each other on the plane thus allows an optical system with a single wavelength to perform stable tracking control and to detect specimen 502.

Detection plate 10 produces a difference between the orbiting distance of the inner circumference and that of the outer circumference. Hence, track region 5 and well 6 provided on the outer circumference may be displaced from those on the inner circumference.

Detection plate 10 may have a learning region having a continuous track groove in a part of detection plate 10. The learning region allows the detection device to detect eccentricity and wobbling of the planes. The learning region allows the detection device to stably scan detection plate 10 with exciting light, thereby increasing the accuracy of detecting specimen 502.

A continuous, spiral groove provided in the inner or outer circumference of detection plate 10 can contain disk information for identifying specific detection plate 10 by playing and recording.

As described above, detection plate 10 includes track region 5 having bottom surface 5A having track groove 505 provided therein, and well 6 having bottom surface 6A apart from track region 5. Bottom surfaces 5A and 6A are disposed on substantially same plane 10P.

Detection plate 10 is configured to be used by irradiating light 601 scanned in the scanning direction (circumferential direction 10A). Track region 5 and well 6 may be arranged in the scanning direction (circumferential direction 10A).

Detection plate 10 may further include projection 11 provided between track region 5 and well 6.

Track region 5, well 6, and projection 11 may be formed by unitary molding.

The offset between bottom surfaces 5A and 6A may be not larger than offset allowance $\Delta z$ defined by a spot diameter $w_0$ of light 601, a wavelength $\lambda$ of light 601, and an allowance value $w(z)$ of the spot diameter of light 601 as:

$$\Delta z = \{(w(z)/w_0)^2 - 1\} \times \pi \times w_0^2 / \lambda.$$

The detection plate may have plural wells 6.

Detection plate 10 may further include flow channel 7 connecting plural wells 6. Bottom surface 6A may be lower than bottom surface 7A of flow channel 7.

The detection plate may have plural track regions 5 and plural wells 6. Each of track regions 5 and respective one of wells 6 constitute respective one of detection regions 2. Detection regions 2 may be arranged in the scanning direction (circumferential direction 10A).

Bottom surface 6A may have groove 506 therein.

Track groove 505 may be at least a part of a spiral groove or concentrically circular grooves.

According to the embodiment, detection plate 10 has a disk shape, but not limited to the shape. Detection plate 10 may have, e.g. substantially a polygonal or elliptical shape. The scanning direction of detection plate 10 changes depending on the shape of detection plate 10. Thus, the scanning direction of detection plate 10 and the scanning optical system are determined by the shape of detection plate 10 and by the specifications of the detection device. Detection plate 10 according to the embodiment has a disk shape, and thus the scanning direction is circumferential direction 10A of detection plate 10, which allows the detection device to have the same configuration as an optical pickup device.

INDUSTRIAL APPLICABILITY

A detection plate according to the present invention allows a detection device with a simple configuration to detect a specimen accurately.

REFERENCE MARKS IN THE DRAWINGS 1 inlet
2 detection region 4 hole
5 track region
5A bottom surface (first bottom surface)
6 well
6A bottom surface (second bottom surface)
7 flow channel
9 cover layer
10 detection plate
10A circumferential direction (scanning direction)
11 projection
505 track groove
601 light

The invention claimed is:

1. A detection plate comprising:
   a substrate having a first surface and a second surface opposite to the first surface; and
   a detection region provided in the first surface of the substrate,
   wherein the detection region includes:
   a track region having a first bottom surface having a track groove provided therein; and
   a well apart from the track region, the well having a second bottom surface, wherein the well is configured to accommodate therein a sample containing specimen, and wherein the entire first bottom surface and the entire second bottom surface are disposed substantially on a single plane.

2. The detection plate of claim 1,
   wherein the detection plate is configured to be used by irradiating light scanned in a scanning direction, and
   wherein the track region and the well are arranged in the scanning direction.

3. The detection plate of claim 1, further comprising a projection provided between the track region and the well.

4. The detection plate of claim 3, wherein the track region, the well, and the projection are formed by integral molding.

5. The detection plate of claim 1,
   wherein the detection plate is configured to be used by irradiating light, and
   wherein an offset between the first bottom surface and the second bottom surface is not larger than an offset allowance $\Delta z$ defined by a spot diameter $w_0$ of the light, a wavelength $\lambda$ of the light, and an allowance value $w(z)$ of the spot diameter of the light as:

$$\Delta z = \{(w(z)/w_0)^2 - 1\} \times \pi \times w_0^2 / \lambda.$$

6. The detection plate of claim 1, wherein the well comprises a plurality of wells.

7. The detection plate of claim 6, further comprising a flow channel connecting the plurality of wells, wherein the second bottom surface is lower than a bottom surface of the flow channel.

8. The detection plate of claim 1,
   wherein the detection plate is configured to be used by irradiating light scanned in a scanning direction,
   wherein the track region comprises a plurality of track regions,
   wherein the well comprises a plurality of wells,
   wherein each of the plurality of track regions and respective one of the plurality of wells constitute respective one of a plurality of detection regions, and
   wherein the plurality of detection regions are arranged in the scanning direction.

9. The detection plate of claim 1, further comprising a cover layer covering the well.

10. The detection plate of claim 1, wherein the well has substantially a circular shape.

11. The detection plate of claim 1, wherein the second bottom surface has a groove provided therein.

12. The detection plate of claim 1, wherein the detection plate has a disk shape.

13. The detection plate of claim 12, wherein the track groove constitutes at least a part of a spiral groove or concentrically circular grooves.

14. The detection plate of claim 1, wherein the first bottom surface of the track region is configured to reflect light.

15. The detection plate of claim 1,
   wherein the first bottom surface of the track region includes lands and a groove provided between the lands, and
   wherein the groove does not reach the well.

16. The detection plate of claim 1,
   wherein the first bottom surface of the track region includes lands and a groove provided between the lands, and
   wherein a bottom of the groove of the first bottom surface of the track region and the second bottom surface of the well are disposed substantially on the plane.

17. The detection plate of claim 1, wherein tracking control of the detection plate is performed according to reflected light which is part of light emitted onto the detection plate and reflected on the first bottom surface of the tracking region.

18. The detection plate of claim 17, wherein the detection plate is configured to detect the specimen contained in the sample with the light emitted onto the detection plate.

* * * * *